United States Patent
Tanaka et al.

(10) Patent No.: US 11,992,587 B2
(45) Date of Patent: May 28, 2024

(54) ELECTRIC BREAST PUMP, METHOD OF CONTROLLING ELECTRIC BREAST PUMP, AND CONTROL PROGRAM FOR ELECTRIC BREAST PUMP

(71) Applicant: PIGEON CORPORATION, Tokyo (JP)

(72) Inventors: Yuichiro Tanaka, Tokyo (JP); Satoru Saito, Tokyo (JP); Sumiko Kuroishi, Tokyo (JP)

(73) Assignee: PIGEON CORPORATION, Tokyo (JP)

( * ) Notice: Subject to any disclaimer, the term of this patent is extended or adjusted under 35 U.S.C. 154(b) by 791 days.

(21) Appl. No.: 16/972,689

(22) PCT Filed: Jun. 7, 2019

(86) PCT No.: PCT/JP2019/022784
§ 371 (c)(1),
(2) Date: Dec. 7, 2020

(87) PCT Pub. No.: WO2019/235625
PCT Pub. Date: Dec. 12, 2019

(65) Prior Publication Data
US 2021/0252200 A1    Aug. 19, 2021

(30) Foreign Application Priority Data

Jun. 8, 2018  (JP) ................................ 2018-110742

(51) Int. Cl.
*A61M 1/06*    (2006.01)
*A61M 1/00*    (2006.01)

(52) U.S. Cl.
CPC ............ *A61M 1/0693* (2021.05); *A61M 1/06* (2013.01); *A61M 1/062* (2014.02);
(Continued)

(58) Field of Classification Search
CPC .............................. A61M 1/06; A61M 1/0693
See application file for complete search history.

(56) References Cited

U.S. PATENT DOCUMENTS 9,162,016 B2 *  10/2015  Geddes ................. A61M 1/069
2017/0080134 A1    3/2017  Makower et al.

FOREIGN PATENT DOCUMENTS

CN    101903054 A    12/2010
JP      5677749 B2     2/2015

OTHER PUBLICATIONS

The extended European search report for the corresponding EP application No. 19815960.0 dated Jan. 20, 2022.

* cited by examiner

*Primary Examiner* — Laura A Bouchelle
(74) *Attorney, Agent, or Firm* — Muncy, Geissler, Olds & Lowe, P.C.

(57) ABSTRACT

An electric breast pump 1 includes a breast placement part 12 at which a breast part including a breast and a nipple of a subject is placed and suction-pressure generating units 10 and 50 that generate a suction pressure in the breast placement part. The suction-pressure generating unit generates a suction cycle including a plurality of different suction pressures. The suction cycle includes basic suction, increased suction with an increased suction pressure, and reduced suction with a reduced suction pressure. A suction pressure difference between a suction pressure increasing in the increased suction and a suction pressure reducing in the reduced suction is an equal pressure and is a pressure difference at a borderline at which a user perceives a change of a suction pressure. In the suction cycle, the basic suction, the increased suction, and the reduced suction are each repeated multiple times consecutively at an equal suction pressure.

6 Claims, 2 Drawing Sheets

(52) U.S. Cl.
CPC ....... *A61M 1/0697* (2021.05); *A61M 1/06935* (2021.05); *A61M 1/74* (2021.05); *A61M 1/75* (2021.05); *A61M 1/82* (2021.05)

ELECTRIC BREAST PUMP, METHOD OF CONTROLLING ELECTRIC BREAST PUMP, AND CONTROL PROGRAM FOR ELECTRIC BREAST PUMP

TECHNICAL FIELD

The present invention relates to an electric breast pump used for pumping milk of, for instance, a mother, a method of controlling the electric breast pump, and a control program for the electric breast pump.

BACKGROUND ART

Conventionally, a breast pump is used when milk is pumped for, for example, a baby by a mother and is stored in a feeding bottle or the like.

Breast pumps include a so-called a "manual breast pump" and an "electric breast pump".

The "manual breast pump" has a lever that swivels in response to an operation by an operator. The lever swivels to generate a negative-pressure space in a main body of the breast pump.

By using this negative-pressure space, milk is drawn and pumped from a breast of a mother.

The "electric breast pump" is not provided with a lever to be operated by an operator, and the pump is driven by the force of a motor or the like, whereby a negative-pressure space is generated in the main body of the breast pump by the pump, and milk is drawn and pumped from a breast of a mother by using this negative-pressure space (for example, PTL 1).

Such an "electric breast pump" is frequently used when mothers who are busy in childcare need to pump a large amount of milk in a minimum time. Thus, in order to pump a large amount of milk in a short period time, the suction pressure of an electric breast pump has to be forcibly increased, resulting in extension of time for pumping milk.

Thus, a conventional electric breast pump is configured to allow a mother, i.e., a user of the breast pump, to freely adjust the intensity and speed of suction.

CITATION LIST

Patent Literature

[PTL 1] Japanese Patent No. 5677749

SUMMARY OF INVENTION

Technical Problem

However, in many cases, the users, e.g., mothers, of electric breast pumps do not know appropriate suction pressure. Thus, it is difficult for them to operate an electric breast pump at, for example, an appropriate suction pressure.

Hence, an object of the present invention is to provide an electric breast pump that allows a user, e.g., a mother, to pump milk at an appropriate suction pressure, a method of controlling the electric breast pump, and a control program for the electric breast pump.

Solution to Problem

The object is attained by an electric breast pump including a breast placement part in which a breast part including a breast and a nipple of a subject is placed and a suction-pressure generating unit that generates a suction pressure in the breast placement part, wherein the suction-pressure generating unit generates a suction cycle including a plurality of different suction pressures, the suction cycle includes basic suction, increased suction with an increased suction pressure, and reduced suction with a reduced suction pressure, a suction pressure difference between a suction pressure increasing in the increased suction and a suction pressure reducing in the reduced suction is an equal pressure and is a pressure difference at a borderline at which a user perceives a change of a suction pressure, and in the suction cycle, the basic suction, the increased suction, and the reduced suction are each repeated multiple times consecutively at an equal suction pressure.

With this configuration, the suction cycle generated by the suction-pressure generating unit includes the basic suction, the increased suction, and the reduced suction and suction pressures of the same kind are successively generated.

Moreover, a suction pressure difference between an increasing pressure in the increased suction and a reducing pressure in the reduced suction is an equal pressure and this pressure corresponds to a pressure difference at a borderline at which a user perceives a change of a suction pressure.

In other words, the suction cycle includes the increased suction and the reduced suction, the increase or reduction thereof changes at the same pressure, and the change serves as a change at a borderline at which a user perceives a change of a suction pressure.

Thus, appropriate fluctuations in suction pressure can suppress pain at a nipple or areola mamma of a user while keeping the efficiency of milk pumping, thereby improving the comfort of use.

Conventionally, suckling by a baby is considered to be ideal on the basis of consideration that the suckling is not an artificial but natural action. Thus, conventional breast pumps have been designed to imitate the suckling by a baby.

However, it has been found that comfort for users, e.g., mothers, in the suction of a breast pump is not necessarily improved only by imitating the sucking action of a baby.

For example, if the pressure fluctuation pattern becomes inappropriate, the efficiency of milk pumping decreases and causes pain and discomfort to users, e.g., mothers, of the breast pump.

For this, in the suction cycle of the configuration, a pattern of "cyclical fluctuation (Yuragi-cycle)" Is implemented. In this case, "cyclical fluctuation" means a suction pattern in which elements of suckling by a baby are extracted and a suction pattern including the elements is regenerated without reducing an amount of pumped milk and without impairing the comfort of use.

In the configuration, the "cyclical fluctuation" stimulates the user with a constant rhythm and relaxes the body of a user.

The relaxing enhances parasympathetic activity and hormone secretion necessary for milk production and milk ejection.

Hence, with this configuration, an electric breast pump can be implemented in which the "suction cycle" that elicits the foregoing effect, and the like, can be automatically activated and users, e.g., mothers, can pump milk at an appropriate suction pressure.

Preferably, the increased suction includes first increased suction with a suction pressure increased from the basic suction and second increased suction with a suction pressure increased from the first increased suction, the reduced suction is suction with a suction pressure reduced from the second increased suction, and in the suction cycle, the basic suction, the first increased suction, the second increased suction, and the reduced suction are each repeated twice.

With this configuration, the basic suction, the first increased suction, the second increased suction, and the reduced suction are each performed twice consecutively.

In contrast to this configuration, if the basic suction, the first increased suction, the second increased suction, and the reduced suction are each generated one time, the effect of a gradual increase in suction pressure is weakened, making it difficult for users, e.g., mothers, to pump milk at an appropriate suction pressure.

Conversely, if the basic suction, the first increased suction, the second increased suction, and the reduced suction are each generated three times, a user may slightly feel "insufficient suction" at a time when low pressures occur successive and feel "pain" at a time when high pressures occur successively.

Regarding this point, if the basic suction, the first increased suction, the second increased suction, and the reduced suction each include two consecutive sucking operations, the electric breast pump makes it possible for users, e.g., mothers, to pump milk at an appropriate suction pressure without causing the foregoing problem.

It is preferable that between a plurality of the suction cycles of the electric breast pump, an interval at which a suction pressure is not generated is formed, and a time of the interval is always same.

With this configuration, the interval is formed between a plurality of the suction cycles, a time when a suction pressure is generated and a time when a suction pressure is not generated are alternatively generated, hence a user is able to pump milk with an appropriate rhythm.

It is preferable that the suction pressure difference of the electric breast pump is 2.5 kPa to 3.5 kPa.

The object is attained by a method of controlling an electric breast pump including a breast placement part in which abreast part including abreast and a nipple of a subject is placed and a suction-pressure generating unit that generates a suction pressure in the breast placement part, the method including: causing the suction-pressure generating unit to generate a suction cycle including basic suction, increased suction with an increased suction pressure, and reduced suction with a reduced suction pressure; with a suction pressure difference between a suction pressure increasing in the increased suction and a suction pressure reducing in the reduced suction being a pressure difference at a borderline at which a user perceives a change of a suction pressure, causing the suction cycle to be generated in which the basic suction, the increased suction, and the reduced suction are each repeated multiple times consecutively at an equal suction pressure.

According to the present invention, the object is attained by a control program for causing an electric breast pump including a breast placement part in which a breast part including breast and a nipple of a subject is placed and including and a suction-pressure generating unit that generates a suction pressure in the breast placement part to execute the control program execute: a function of generating a suction cycle including basic suction, increased suction with an increased suction pressure, and reduced suction with a reduced suction pressure; a function of setting a suction pressure difference between a suction pressure increasing in the increased suction and a suction pressure reducing in the reduced suction to a pressure difference at a borderline at which a user perceives a change of a suction pressure; and a function of generating the suction cycle in which the basic suction, the increased suction, and the reduced suction are each repeated multiple times consecutively at an equal suction pressure.

Advantageous Effects of Invention

The present invention can advantageously provide an electric breast pump that allows users, e.g., mothers, to pump milk with an appropriate suction pressure, a method of controlling the electric breast pump, and a control program for the electric breast pump.

DESCRIPTION OF EMBODIMENTS

A preferred embodiment of the present invention will be specifically described below with reference to the accompanying drawings.

The following embodiment is a preferred specific example of the present invention and thus is technically limited in preferred ways. The scope of the present invention is not limited to these modes unless the present invention is limited in the following description.

Figure 1:
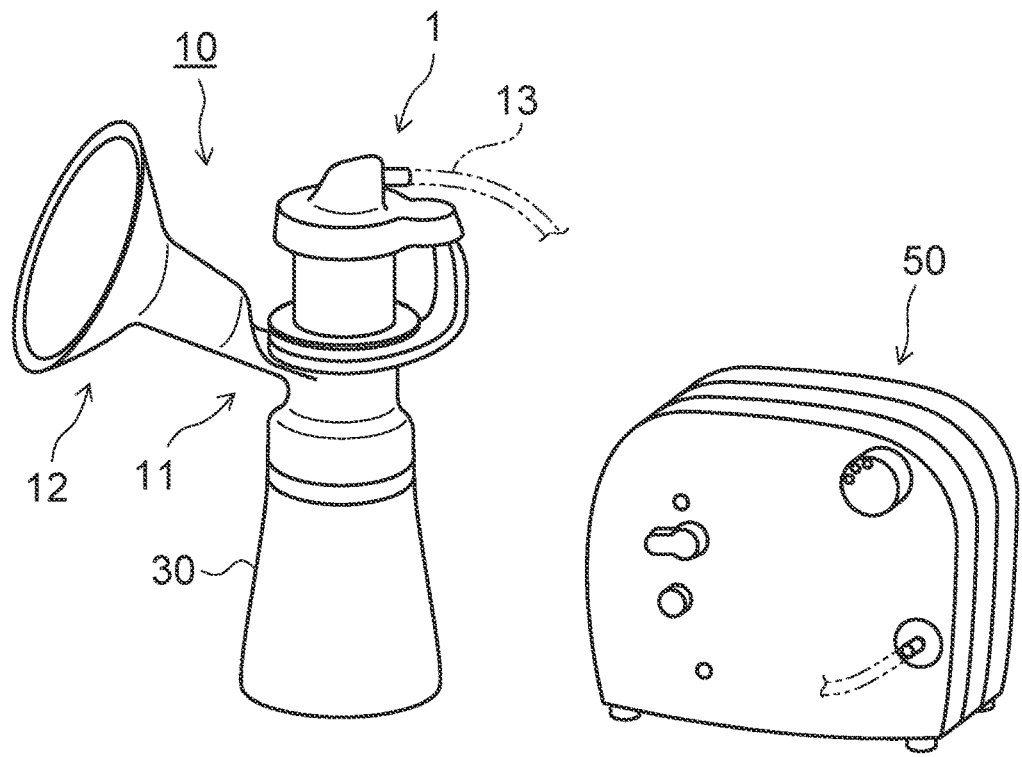
FIG. 1 is a schematic diagram illustrating the principal configuration of an electric breast pump according to the present invention.

FIG. 1 is a schematic diagram illustrating the principal configuration of an electric breast pump 1 according to the present invention.

As illustrated in FIG. 1, the electric breast pump 1 includes a breast pump 10 and a pump unit 50. The breast pump 10 and the pump unit 50 are connected to each other via a tube 13.

Moreover, as illustrated in FIG. 1, the breast pump 10 includes a breast-pump body 11, a bottle 30, and a breast placement part 12 where a breast of a mother, a user of the electric breast pump 1, is placed.

Figure 2:
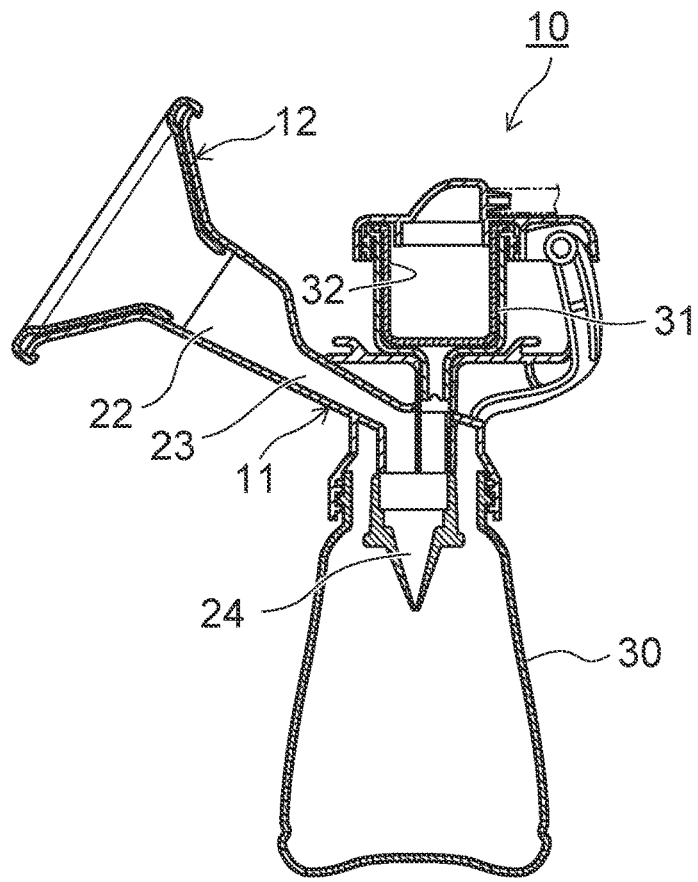
FIG. 2 is a schematic cross-sectional view illustrating the internal structure and the like of the breast pump.

FIG. 2 is a schematic cross-sectional view illustrating the internal structure of the breast pump 10.

As illustrated in FIG. 2, the breast pump 10 has a case 31. In the case 31, a deformable member 32 that is able to change a shape thereof is disposed.

The pump unit 50 in FIG. 1 is started to rotate a motor provided in the pump unit 50, a negative pressure in the cylinder of the unit 50 changes, and the change is conveyed to the deformable member 32 via the tube 13, and an air pressure in the deformable member 32 decreases to deform the deformable member 32.

When the volume of the deformable member 32 considerably decreases in the case 31 as described above, an air pressure is largely reduced in an enclosed space 23 communicating with a space between the deformable member 32 and the case 31.

Specifically, when a negative pressure increases in the enclosed space 23, milk is sucked from a breast placed in the breast placement part 12 of FIG. 2, and the pumped milk passes through an air passage 22 and is stored in the bottle 30 via a small chamber 24.

Thus, the breast-pump body 11 and the pump unit 50 or the like are examples of a suction-pressure generating unit for generating a suction pressure in the breast placement part 12.

(Operation Example of Electric Breast Pump 1)

In the following example, a mother pumps milk for a baby by using the electric breast pump 1 according to the present embodiment.

First, the mother who are to extract milk inserts her breast into the breast placement part 12 of the breast pump 10 in FIG. 1 and places her breast therein.

Subsequently, the switch of the pump unit 50 in FIG. 2 is operated to select a desired suction pressure.

As the suction pressure, a first suction pressure is selected in a range from, for example, −10 kPa to −31 kPa by a mother who is a user of the breast pump.

In the example of the present embodiment, a mother selects, for example, −10 kPa or −31 kPa as a starting pressure of a suction pressure.

Figure 3:
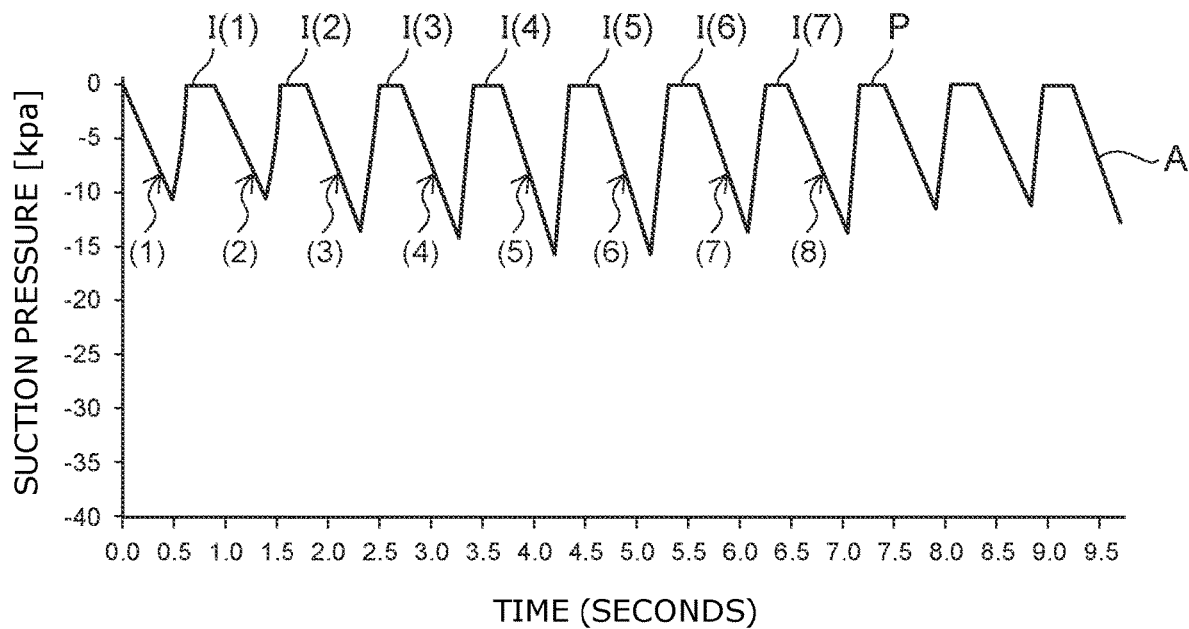
FIG. 3 is a schematic explanatory drawing indicating the suction pressures of the electric breast pump when −10 kPa is selected as a starting pressure of a suction pressure, and indicates, for example, "pressure-fluctuation suction pattern" as a suction cycle of the suction pressures.

FIG. 3 is a schematic explanatory drawing indicating the suction pressures of the electric breast pump 1 when −10 kPa is selected as a starting pressure of a suction pressure, and indicates, for example, "pressure-fluctuation suction pattern" as a suction cycle of the suction pressures.

Figure 4:
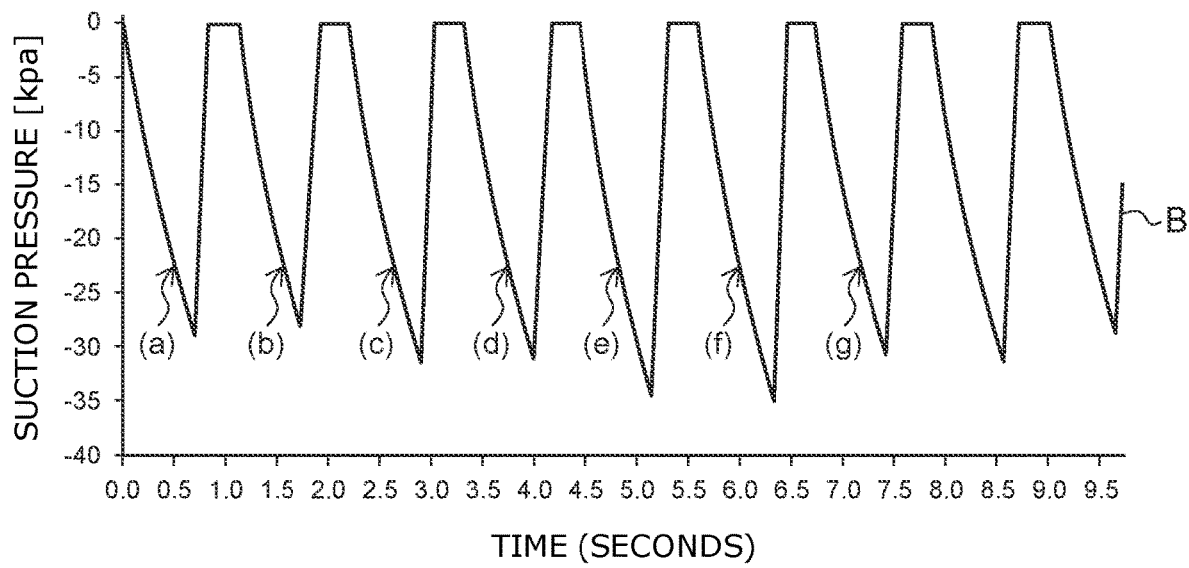
FIG. 4 is a schematic explanatory drawing indicating the suction pressures of the electric breast pump when −31 kPa is selected as a starting pressure of a suction pressure, and indicates, for example, "pressure-fluctuation suction pattern" of the suction pressures.

FIG. 4 is a schematic explanatory drawing indicating the suction pressures of the electric breast pump 1 when −31 kPa is selected as a starting pressure of a suction pressure, and indicates, for example, "pressure-fluctuation suction pattern" of the suction pressures.

In "pressure-fluctuation suction pattern" of FIG. 3, one cycle includes eight sucking operations and is set at 7.5 seconds to 13.2 seconds.

Moreover, FIG. 3 indicates the suction cycle of "pressure-fluctuation suction pattern A" that includes eight sucking operations starting from −10 kPa.

Moreover, FIG. 4 indicates the suction cycle of "pressure-fluctuation suction pattern B" that includes eight sucking operations starting from −31 kPa.

A specific explanation will be given below.

The example of "pressure-fluctuation suction pattern A" will be first described below.

At the start of an operation of the electric breast pump 1, the suction of "pressure-fluctuation suction pattern A" is started and suction (1) is generated as a basic suction.

The suction (1) has a suction pressure of −10 kPa.

Moreover, the suction time of the suction (1) is, for example, about 0.7 seconds. The suction time is set constant at least at the same suction pressure.

After the suction, intervals having no generated suction pressures are provided. In FIG. 3, seven intervals I(1) to I(7) are provided.

The seven intervals I(1) to (7) are all set at an equal time, for example, 0.15 seconds to 0.25 seconds.

After the suction (1), suction (2) of a basic suction is generated through the interval I(1) at the same suction pressure (−10 kPa) as the suction (1).

In other words, the basic suctions are successively performed.

Subsequently, suction (3) as first increased suction is generated through the interval I(2).

The suction pressure of the suction (3) is, for example, −13 kPa that is higher than the suction pressures (−10 kPa) of the suction (1) and the suction (2) as the basic suctions by 3 kPa.

The pressure increase may vary from 2.5 kPa to 3.5 kPa but is preferably set at 3 kPa.

The suction pressure is set at 3 kPa for the following reason.

The pressure increase of 3 kPa is the borderline of a change of comfort for a mother who uses the electric breast pump 1. If the pressure difference is larger than 3 kPa, for example, the pressure difference is set at 6 kPa, a mother may feel pain and may feel insufficient suction at a low pressure. In other words, because of an extremely large difference between a low pressure and a high pressure, the mother may feel a low pressure is too low relative to a high pressure and may feel that a high pressure causes pain relative to a low pressure, leading to difficulty in adjustment to an appropriate pressure.

In the case of a pressure difference smaller than 3 kPa, for example, a pressure difference of about 2 kPa, a mother may hardly feel a pressure and thus feel "insufficient suction".

This is not because "a pressure is hardly felt" but because a change of pressure is hardly felt. "Insufficient suction" results from the absence of perception of "fluctuation".

After that, suction (4) is generated through the interval I(3) at the same suction pressure as the suction (3).

Subsequently, suction (5) as second increased suction is generated through the interval I(4).

The suction pressure of the suction (5) is, for example, −16 kPa that is higher than the suction pressures (−13 kPa) of the suction (3) and the suction (4) as the first increased suctions by 3 kPa.

This provides appropriate fluctuations in pressure for a mother, a user of the breast pump.

An equal suction pressure is generated twice consecutively for the following reason.

If each suction pressure is increased, the suction pressure is not gradually increased but is rapidly increased. This may discomfort a mother.

Conversely, if an equal suction pressure is applied, for example, five times and then the pressure is increased, a mother may feel "insufficient suction" at a low pressure and may feel pain at a high pressure because the high pressure is applied five times consecutively.

Thus, in the present embodiment, an equal suction pressure is generated twice consecutively and then the suction pressure is changed.

After the suction (5), suction (6) is generated through the interval I(5).

The suction (6) has a suction pressure of −16 kPa equal to that of the suction (5).

Subsequently, suction (7) as reduced suction is generated through the interval I(6).

The suction pressure of the suction (7) is, for example, −13 kPa that is lower than the suction pressures (−16 kPa) of the suction (5) and the suction (6) as the second increased suctions by 3 kPa.

This provides appropriate fluctuations in pressure for a mother, a user of the breast pump.

After the suction (7), suction (8) is generated through interval I(7).

The suction (8) has a suction pressure of −13 kPa equal to that of the suction (7).

In this way, one cycle of "pressure-fluctuation suction pattern A" is completed and then the same "pressure-fluctuation suction pattern A" is started.

At this point, the subsequent "pressure-fluctuation suction pattern A" is started through a pose P that is an interval.

The pose P is a part where a suction pressure is not applied and a sucking operation is not performed.

The pose P is provided between the cycles of "pressure-fluctuation suction pattern A" and is kept at the same width (time).

In the present embodiment, the pose P and the intervals I(1) to (7) are provided so as to alternatively generate a time when a suction pressure is generated and a time when a suction pressure is not generated.

As described above, one cycle of "pressure-fluctuation suction pattern A" in FIG. 3 is performed and is repeated a required number of times, allowing users, e.g., mothers, to extract milk.

Hence, the present embodiment can obtain the following effects.

In the present embodiment, a suction pressure is gradually increased by 3 kPa to a maximum pressure without a rapid increase. Thus, the nipples and areola mammae of users, e.g., mothers, are not rapidly stretched and the burden can be reduced.

The frequency at which suction pressure is maximized is reduced to one forth (two times in eight sucking operations) and the suction pressure is appropriately reduced suitably, achieving comfortable pumping of milk.

Furthermore, for example, "pressure-fluctuation suction pattern A" with an appropriate differential pressure of 3 kPa is a "cyclical fluctuation" for providing "fluctuation (Yuragi)" for a mother, preventing uncomfortable use by a mother.

In the present embodiment, suction fluctuates and a monotonous rhythm is not provided. Thus, the suction of "pressure-fluctuation suction pattern A" is an appropriate "cyclical fluctuation", thereby providing comfortable feeling for a mother.

A mother can feel a rhythm of inhalation and rest, thereby comfortably extracting milk in a relaxed state.

Moreover, for a mother who frequently uses the electric breast pump 1 for pumping milk several times for a long time every day, the present embodiment can reduce an excessive long-time stretch of a nipple and prevent swelling of a nipple.

Even if a mother is a beginner of the electric breast pump 1 and is not used to stretching a nipple with suction, the present embodiment allows the mother to become used to a suction pressure of milk pumping as gentle suction.

Conventionally, suckling of a baby is regarded as being ideal because suckling is a natural action and is not artificial. Thus, conventional breast pumps have been intended to imitate suckling of a baby.

However, it is understood that comfort for users, e.g., mothers, is not always improved as the suction of an electric breast pump only by imitating the suction of a baby.

If the pressure-fluctuation suction pattern become inappropriate, the efficiency of milk pumping decreases and causes pain and discomfort to a mother who uses the breast pump.

Regarding this point, "pressure-fluctuation suction pattern A" achieves a pattern of "fluctuation (Yuragi)". In this case, "fluctuation (Yuragi)" means a suction cycle in which the elements of suckling of a baby are extracted and a suction pattern including the elements is regenerated without reducing an amount of milk pumping and the comfort of use.

As described above, in the present embodiment, "cyclical fluctuation" stimulates a mother with a certain rhythm and relaxes the body of a user.

Moreover, the relaxing increases parasympathetic activity and enhances hormone secretion necessary for milk production and milk ejection.

Thus, the electric breast pump 1 can automatically operate "pressure-fluctuation suction pattern A" that obtains the foregoing effect and pump milk with an appropriate suction pressure for users, e.g., mothers.

"Pressure-fluctuation suction pattern B" in FIG. 4 is substantially identical to "pressure-fluctuation suction pattern A" except for a suction pressure starting from −29 kPa and a suction time.

In the present embodiment, as illustrated in FIGS. 3 and 4, the basic suction, the first increased suction, the second increased suction, and the reduced suction are each generated twice consecutively in one cycle. The present invention is not limited to this cycle and other cycles may be used as follows.

1) Suction Cycle of Three Consecutive Times

In this cycle, unlike in the embodiment, the basic suction, the first increased suction, the second increased suction, and the reduced suction are each performed three times consecutively in one cycle.

2) Suction Cycle of Twice and Three Times

In this cycle, unlike in the embodiment, the basic suction is performed twice consecutively and then is performed three times consecutively.

Thereafter, the second increased suction is performed twice consecutively and then the reduced suction is performed three times consecutively, completing one cycle.

3) Suction Cycle Including Third Increased Suction and Second Reduced Suction

In this cycle, unlike in the embodiment, the basic suction is performed twice consecutively and then the first increased suction is performed twice consecutively.

Thereafter, the second increased suction is performed twice consecutively and then third increased suction with an increased suction pressure is performed twice consecutively.

Thereafter, the first reduced suction with a reduced suction pressure is performed and then the second reduced suction with a further reduced suction pressure is performed twice consecutively, completing one cycle.

In the present embodiment, the present invention is implemented as, but is not limited to, an apparatus. The present invention may be a program executable by a computer and may be distributed while being stored in storage media including a magnetic disk (e.g., a floppy (registered trademark) disk or a hard disk), an optical disk (CD-ROM or DVD), a magneto-optical disk (MO), and semiconductor memory.

Any storage medium capable of storing programs and readable by a computer may be used. The storage format of the storage medium is not particularly limited.

Furthermore, processing for implementing the present embodiment may be partially performed by an OS (operating system) that operates on a computer in response to an instruction of a program installed on the computer from a storage medium and MW (middleware) including database management software and network software.

Moreover, the storage medium in the present invention is not limited to a medium independent of a computer. A storage medium for storage or temporary storage of a program transmitted and downloaded through a LAN or the Internet may be used.

The computer in the present invention may be any computer that performs processing in the present embodiment based on a program stored in a storage medium. An apparatus including a personal computer or a system including multiple apparatuses connected via a network may be used.

Alternatively, the computer in the present invention is not limited to a personal computer. The present invention also includes an arithmetic processing unit included in an information processor, and a microcomputer. A computer is a general name of equipment or an apparatus that can implement the functions of the present invention by means of programs.

In the foregoing explanation, the embodiment of the present invention was described. However, the present invention is not limited to the embodiment and can be changed in various ways within the scope of the claims. The configuration of the embodiment may be partially omitted or optionally combined with a different configuration.

REFERENCE SIGNS LIST

1 Electric breast pump
10 Breast pump
11 Breast-pump body
12 Breast placement part
13 Tube
222 Air passage
23 Enclosed space
24 Small chamber
30 Bottle
31 Case
32 Deformable member
50 Pump unit

The invention claimed is:

1. An electric breast pump comprising:
a breast placement part in which a breast part including a breast and a nipple of a subject is placed; and
a suction-pressure generating unit that generates a suction pressure in the breast placement part, wherein
the suction-pressure generating unit generates a suction cycle including a plurality of different suction pressures,
the suction cycle includes basic suction, increased suction with an increased suction pressure, and reduced suction with a reduced suction pressure,
a suction pressure difference between a suction pressure increasing in the increased suction and a suction pressure reducing in the reduced suction is an equal pressure and is a pressure difference at a borderline at which a user perceives a change of a suction pressure,
in the suction cycle, the basic suction, the increased suction, and the reduced suction are each repeated multiple times consecutively at an equal suction pressure, and
the suction pressure difference is 2.5 kPa to 3.5 kPa.

2. The electric breast pump according to claim 1, wherein
the increased suction includes first increased suction with a suction pressure increased from the basic suction and second increased suction with a suction pressure increased from the first increased suction,
the reduced suction is suction with a suction pressure reduced from the second increased suction, and
in the suction cycle, the basic suction, the first increased suction, the second increased suction, and the reduced suction are each repeated twice.

3. The electric breast pump according to claim 2, wherein between a plurality of the suction cycles, an interval at which a suction pressure is not generated is formed, and a time of the interval is always same.

4. A method of controlling an electric breast pump including a breast placement part in which a breast part including a breast and a nipple of a subject is placed, and a suction-pressure generating unit that generates a suction pressure in the breast placement part, the method comprising:
causing the suction-pressure generating unit to generate a suction cycle including basic suction, increased suction with an increased suction pressure, and reduced suction with a reduced suction pressure;
with a suction pressure difference between a suction pressure increasing in the increased suction and a suction pressure reducing in the reduced suction being a pressure difference at a borderline at which a user perceives a change of a suction pressure,
causing the suction cycle to be generated in which the basic suction, the increased suction, and the reduced suction are each repeated multiple times consecutively at an equal suction pressure, and
the suction pressure difference is 2.5 kPa to 3.5 kPa.

5. A non-transitory computer readable medium with a control program for causing an electric breast pump including a breast placement part in which a breast part including a breast and a nipple of a subject is placed and a suction-pressure generating unit that generates a suction pressure in the breast placement part to execute:
a function of generating a suction cycle including basic suction, increased suction with an increased suction pressure, and reduced suction with a reduced suction pressure;
a function of setting a suction pressure difference between a suction pressure increasing in the increased suction and a suction pressure reducing in the reduced suction to a pressure difference at a borderline at which a user perceives a change of a suction pressure;
a function of generating the suction cycle in which the basic suction, the increased suction, and the reduced suction are each repeated multiple times consecutively at an equal suction pressure;
the suction pressure difference is 2.5 kPa to 3.5 kPa.

6. An electric breast pump comprising:
a breast placement part in which a breast part including a breast and a nipple of a subject is placed; and
a suction-pressure generating unit that generates a suction pressure in the breast placement part, wherein
the suction-pressure generating unit generates a suction cycle including a plurality of different suction pressures,
the suction cycle includes basic suction, increased suction with an increased suction pressure, and reduced suction with a reduced suction pressure,
a suction pressure difference between a suction pressure increasing in the increased suction and a suction pressure reducing in the reduced suction is an equal pressure and is a pressure difference at a borderline at which a user perceives a change of a suction pressure,
in the suction cycle, the basic suction, the increased suction, and the reduced suction are each repeated multiple times consecutively at an equal suction pressure,
the increased suction includes first increased suction with a suction pressure increased from the basic suction and second increased suction with a suction pressure increased from the first increased suction,
the reduced suction is suction with a suction pressure reduced from the second increased suction, and in the suction cycle, the basic suction, the first increased suction, the second increased suction, and the reduced suction are each repeated twice.

\* \* \* \* \*